United States Patent
Gould et al.

(10) Patent No.: US 7,090,803 B1
(45) Date of Patent: Aug. 15, 2006

(54) LATERAL FLOW IMMUNOASSAY DEVICE

(75) Inventors: Martin Gould, Mullica Hill, NJ (US);
Yli Remo Vallejo, Newark, DE (US);
Robert Bernstine, Chesapeake City, MD (US)

(73) Assignee: American Bio Medica Corporation, Kinderhook, NY (US)

( * ) Notice: Subject to any disclaimer, the term of this patent is extended or adjusted under 35 U.S.C. 154(b) by 0 days.

(21) Appl. No.: 10/695,145

(22) Filed: Oct. 28, 2003

(51) Int. Cl.
*G01N 22/00* (2006.01)

(52) U.S. Cl. .................. 422/58; 422/50; 422/55; 422/56; 422/68.1; 436/518; 436/529; 436/530; 436/164; 436/166; 436/165; 435/7.1; 435/174; 435/283.1; 435/287.2

(58) Field of Classification Search .......... 422/50, 422/56, 55, 61, 68.1, 69, 70; 435/4, 7.1, 435/7.94, 174, 283.1, 287.1, 287.2, 287.7, 435/288.2, 288.7; 436/161, 162, 518, 501, 436/529, 528
See application file for complete search history.

(56) References Cited

U.S. PATENT DOCUMENTS

| | | | |
|---|---|---|---|
| 4,786,471 A * | 11/1988 | Jones et al. ............... 422/61 |
| 4,846,005 A * | 7/1989 | Bacehowski et al. .... 73/864.81 |
| 4,857,453 A * | 8/1989 | Ullman et al. ........... 435/7.92 |
| 4,943,522 A * | 7/1990 | Eisinger et al. ........... 435/7.25 |
| 4,965,047 A * | 10/1990 | Hammond ................. 422/58 |
| 5,204,063 A * | 4/1993 | Allen .................... 422/58 |
| 5,260,031 A | 11/1993 | Seymour |
| 5,268,148 A * | 12/1993 | Seymour ................ 422/101 |
| 5,283,038 A | 2/1994 | Seymour |
| 5,290,518 A * | 3/1994 | Johnson ................ 422/58 |
| 5,364,598 A * | 11/1994 | Oxley ................... 422/102 |
| 5,376,337 A | 12/1994 | Seymour |
| 5,380,492 A | 1/1995 | Seymour |
| 5,393,496 A | 2/1995 | Seymour |
| 5,489,414 A * | 2/1996 | Schreiber et al. .......... 422/64 |
| 5,510,266 A * | 4/1996 | Bonner et al. ............. 436/43 |
| 5,591,401 A * | 1/1997 | Sayles ................... 422/58 |
| 5,630,986 A * | 5/1997 | Charlton et al. ........... 422/64 |
| 5,645,798 A * | 7/1997 | Schreiber et al. .......... 422/58 |
| 5,695,930 A | 12/1997 | Weinstein et al. |
| 5,726,064 A * | 3/1998 | Robinson et al. ......... 436/514 |

(Continued)

OTHER PUBLICATIONS

Schramm et al; "A simple saliva-based test for detecting antibodies to human immunodeficiency Virus" Jul. 1999, pp. 577-580; vol. 6, No. 4; Clinical and Diagnostic Laboratory Immunology.

*Primary Examiner*—Long V. Le
*Assistant Examiner*—Melanie Yu
(74) *Attorney, Agent, or Firm*—B. Aaron Schulman; Stites & Harbison, PLLC

(57) ABSTRACT

A lateral flow immunoassay test device that includes a housing with an elongated slot for holding a test sample collector; an elongated holder member for securing at least one immunoassay test strip therein; a first chamber for storing a first, pre-treatment reagent; and a second chamber for storing a second reagent. The pre-treatment reagent is contained within a rupturable enclosure. A piercing member is located within the housing that is used to rupture the enclosure in order to release the pre-treatment reagent so that the sample and pre-treatment reagent form a mixture. The second reagent may then be introduced to the mixture which is allowed to react with the second reagent for a period of time. The mixture and second reagent combination is then contacted with the immunoassay test strip.

27 Claims, 5 Drawing Sheets

U.S. PATENT DOCUMENTS

| | | | |
|---|---|---|---|
| 5,830,410 A * | 11/1998 | Thieme et al. | 422/58 |
| 5,935,864 A * | 8/1999 | Schramm et al. | 436/174 |
| 5,965,453 A * | 10/1999 | Skiffington et al. | 436/165 |
| 5,989,499 A * | 11/1999 | Catanzariti et al. | 422/63 |
| 6,214,629 B1 * | 4/2001 | Freitag et al. | 436/518 |
| 6,267,722 B1 * | 7/2001 | Anderson et al. | 600/300 |
| 6,277,646 B1 * | 8/2001 | Guirguis et al. | 436/165 |
| 6,300,068 B1 * | 10/2001 | Burg et al. | 435/6 |
| 6,410,275 B1 * | 6/2002 | Kluttz et al. | 435/91.1 |
| 6,464,939 B1 * | 10/2002 | Bachand et al. | 422/58 |
| 6,528,632 B1 * | 3/2003 | Catanzariti et al. | 536/23.1 |
| 6,634,243 B1 * | 10/2003 | Wickstead et al. | 73/863.23 |
| 6,887,681 B1 * | 5/2005 | DiCesare et al. | 435/30 |
| 2002/0160428 A1 * | 10/2002 | Sundrehagen | 435/7.9 |
| 2003/0064526 A1 * | 4/2003 | Niedbala et al. | 436/165 |
| 2003/0148752 A1 * | 8/2003 | Chen | 455/343 |
| 2004/0048395 A1 * | 3/2004 | Lee et al. | 436/514 |
| 2004/0082878 A1 * | 4/2004 | Baldwin et al. | 600/573 |

* cited by examiner

LATERAL FLOW IMMUNOASSAY DEVICE

BACKGROUND OF THE INVENTION

The present invention is directed toward a lateral flow immunoassay device and more particularly, toward a test device that allows the sample to be treated and incubated prior to being introduced to the test strip.

Immunoassay devices utilizing immunochromatography are often single step devices where a test sample is analyzed for the presence of certain analytes. For example, a specified volume of the sample is contacted with one end of a test strip. The test strip contains colored particles coated with a binder dried on the strip. As the sample is wicked up the test strip, the analyte in the sample reacts with the binder coated on the particles. The test strip also contains antigens in discrete zones. As the reaction mixture flows up the strip, any reaction between the antigens and the analyte, if present, may be observed by the appearance or non-appearance of color in the zones. Often, such tests are used in drug screening.

There are several disadvantages to the system described above. For example, once the test sample is introduced, there is no user control over the subsequent events. That is, the fluid flow determines the speed and timing of all of the reactions. Also, if the sample requires pre-treatment with specific reagents to dilute or denature interferants, modify analyte structure, or release analyte from binders, such treatments must be performed outside of the confines of the test device. Therefore, a need exists for a self-contained and simple to use test device that allows control over the test sample so that more accurate test results may be obtained.

SUMMARY OF THE INVENTION

The present invention is designed to overcome the deficiencies of the prior art discussed above. It is an object of the present invention to provide a self-contained test device that allows the test sample to be pre-treated and pre-incubated.

It is another object of the present invention to provide a test device that allows the test sample to flow onto the test strip easily and increases the sensitivity of the assay.

In accordance with the illustrative embodiments demonstrating features and advantages of the present invention, there is provided a lateral flow immunoassay test device that includes a housing with an elongated slot for holding a test sample collector; an elongated holder member for securing at least one immunoassay test strip therein; a first chamber for storing a first, pre-treatment reagent; and a second chamber for storing a second reagent such as a binder. The pre-treatment reagent is contained within a rupturable enclosure or receptacle which may be in the form of a bladder. A piercing member is located within the housing that is used to rupture the enclosure in order to release the pre-treatment reagent so that the sample and pre-treatment reagent form a mixture. The binder may then be introduced to the mixture which is allowed to react with the binder for a period of time. The mixture and binder combination is then contacted with the immunoassay test strip.

In one embodiment a button is located in the front side of the housing. When the button is depressed, the piercing member is forced into the enclosure which releases the pre-treatment reagent contained therein. The sample collector is inserted into the housing so that the test sample is placed into contact with the pre-treatment reagent and the sample and pre-treatment reagent mix. The mixture combines with the binder in the manner described above before contacting the test strip.

In a second embodiment the sample collector is aligned with the piercing member within the housing. Force is applied to the sample collector which forces the piercing member into contact with the rupturable enclosure, thereby piercing the enclosure. This action, in turn, causes the enclosure to burst so that the pre-treatment reagent is released. The test sample flows through holes formed in the piercing member and mixes with the first reagent. The mixture than combines with the binder in the manner described above before contacting the test strip.

In a further embodiment the housing is generally L-shaped with a vertical leg and a horizontal leg extending from the bottom of the vertical leg. The immunoassay test strip is located within the vertical leg. The test sample and first reagent, being mixed as described above, is contacted with the binder in the horizontal leg. In order for the mixture and binder combination to contact the test strip, the housing must be tilted backward so that the vertical leg of the housing becomes the horizontal leg and the horizontal leg becomes the vertical leg. The mixture and binder combination may now flow onto the test strip.

Other objects, features, and advantages of the invention will be readily apparent from the following detailed description of preferred embodiments thereof taken in conjunction with the drawings.

BRIEF DESCRIPTION OF THE DRAWINGS

For the purpose of illustrating the invention, there is shown in the accompanying drawings forms that are presently preferred; it being understood that the invention is not intended to be limited to the precise arrangements and instrumentalities shown.

DETAILED DESCRIPTION OF THE PREFERRED EMBODIMENTS

Figure 1:
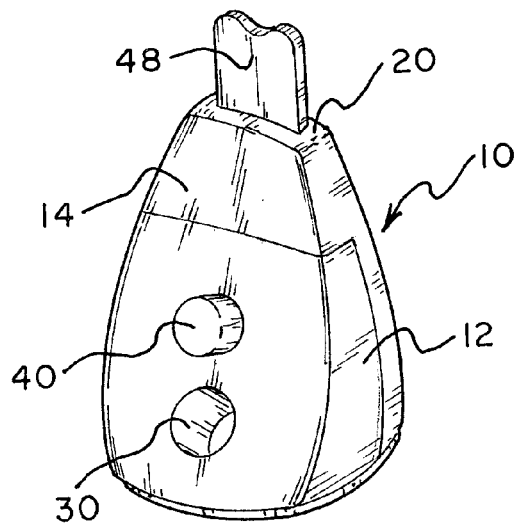
FIG. 1 is a front perspective view of a first embodiment of the present invention.

Referring now to the drawings in detail wherein like reference numerals have been used throughout the various figures to designate like elements, there is shown in FIG. 1 a lateral flow immunoassay device constructed in accordance with the principles of the present invention and designated generally as 10.

Figure 3:
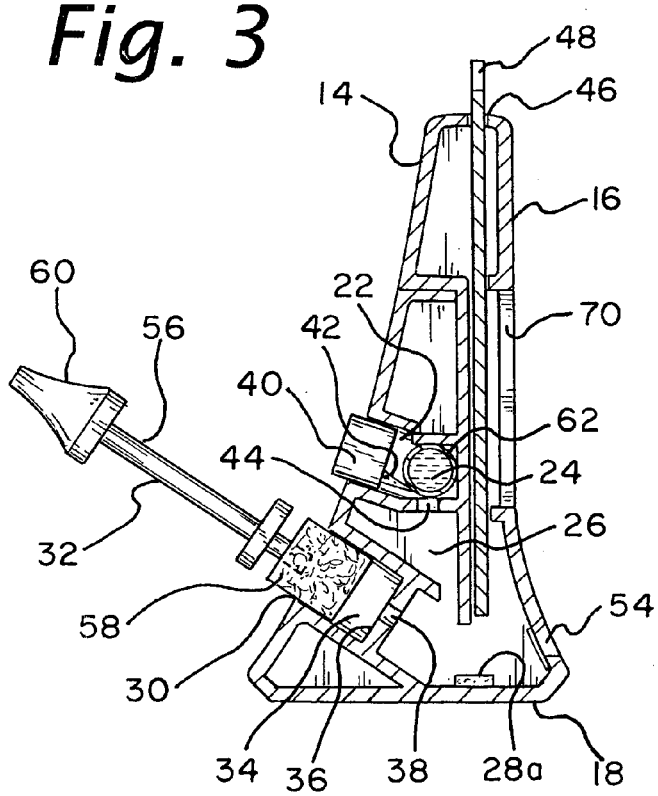
FIG. 3 is a cross-sectional view of the first embodiment of the present invention.
Figure 4:
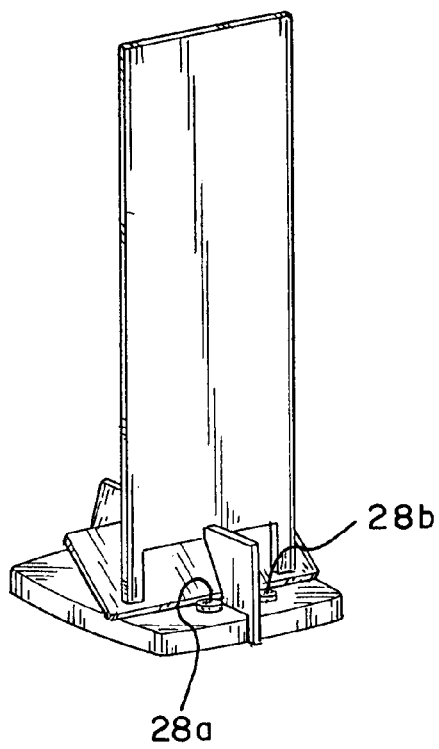
FIG. 4 is a rear perspective view of the interior of the housing of the first embodiment of the present invention.

A first embodiment of the present invention is shown in FIG. 1. The lateral flow immunoassay device essentially includes a housing 12 with a front side 14, a rear side 16, a bottom 18, and a top 20. The housing 12 also includes a first chamber 22 for storing a first, pre-treatment reagent 24 and a second chamber 26 for storing a second reagent 28a and 28b. (See FIGS. 3 and 4.) Located within the front side 14 of the housing 12 is at least one opening 30 through which a test sample collector 32 may be slidably mounted. The opening 30 leads into an elongated slot 34 with a substantially closed bottom end 36. However, formed within the closed bottom end 36 is an opening 38 that allows for fluid communication with the second chamber 26.

Figure 2:
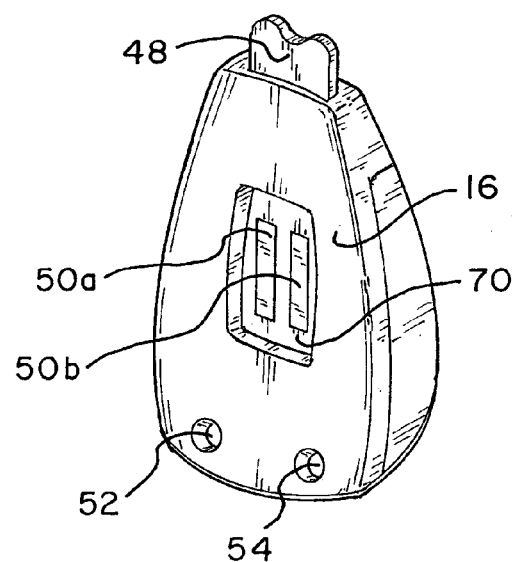
FIG. 2 is a rear perspective view of the first embodiment of the present invention.

Also located in the front side 14 of the housing 12 is means 40 for activating the pre-treatment reagent 24. The activating means 40 fits within the first chamber 22 and may be in the form of a button. Located at the bottom of the first chamber 22 is at least one aperture 44 which enables the first chamber 22 to be in fluid communication with the second chamber 26. The operation of this button will be discussed in greater detail below. Located in the top 20 of the housing 12 is an elongated slit 46 through which an elongated holder member 48 for securing immunoassay test strips 50a and 50b may be slidably mounted. The rear side 16 of the housing 12 has a plurality of widows 52 and 54 through which it may be observed whether there is a sufficient amount of the sample mixed with the first reagent and second reagent to be wicked up the test strips. (See FIG. 2.)

The sample collector 32 may include an elongated member 56 with a swab or sponge 58 located at one end and a handle 60 located at the opposite end. The pre-treatment reagent may be a standard buffer and is contained within a rupturable enclosure in the form of a bladder 62. The second reagent may be an antigen or a binder such as a colloidal gold-antibody complex, for example.

In order to use the device, a test sample is collected on the sponge 58. The collector 32 is then inserted through the opening 30 and into the slot 34. As the sponge 58 is forced through the slot 34, it contacts the opening 38 located at the bottom end 36 of the slot 34. The test sample is forced through the opening 38 and into the second chamber 26. Pressure is then applied to the button 40. Alternatively, the button may be depressed simultaneously with, or before, the sponge is inserted through the slot. Attached to the button 40 is a piercing member 42 that, as force is continued to be placed on the button 40, comes into contact with the rupturable enclosure 62 and ruptures it. The buffer flows through the aperture 44 located at the bottom of the first chamber 22. Sample flows through the opening 38 and mixes with the buffer 24. By adding the buffer to the sample, the buffer allows the sample to flow more easily, thereby increasing the accuracy of the test results.

Figure 5:
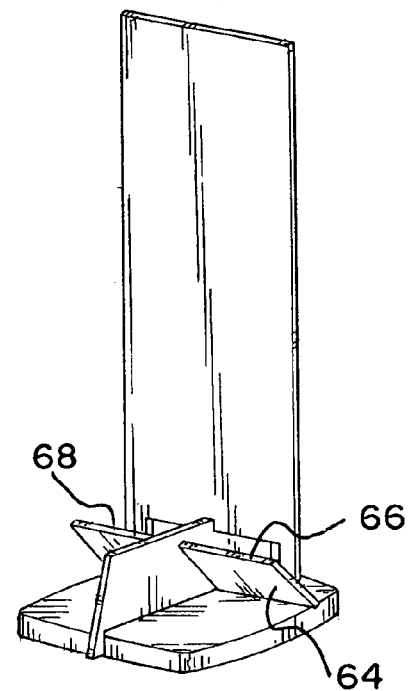
FIG. 5 is a front perspective view of the interior of the housing of the first embodiment of the present invention.

The sample and buffer then flow into the second chamber 26 which is located adjacent the bottom 18 of the housing 12. The second chamber 26 may have a partition 64 so that two separate compartments 66 and 68 are formed therein with a second reagent 28a and 28b located in a respective compartment 66 and 68. (See FIGS. 4 and 5.) The partition 64 is formed in such a manner so that the sample and buffer mixture is split into the two compartments 66 and 68. The second reagent is introduced to the mixture and is allowed to react for a period of time. That is, the reagent and mixture combination is incubated for a period of time.

Next, the elongated holder member 48 containing the test strips 50a and 50b is inserted through the slit 46 and slid downwardly, toward the bottom 18 of the housing 12. The test strips 50a and 50b are typical prior art test strips where various antigens are dried thereon that compete with the analyte being tested for a binding site on the antibody. The slit 46 is in fluid communication with the second chamber 26 so that the test strips 50a and 50b are forced into contact with the mixture and second reagent combination as it is pushed toward the bottom 18 of the housing 12. Any reactions on the test strips 50a and 50b may be observed through the window 70.

Figure 6:
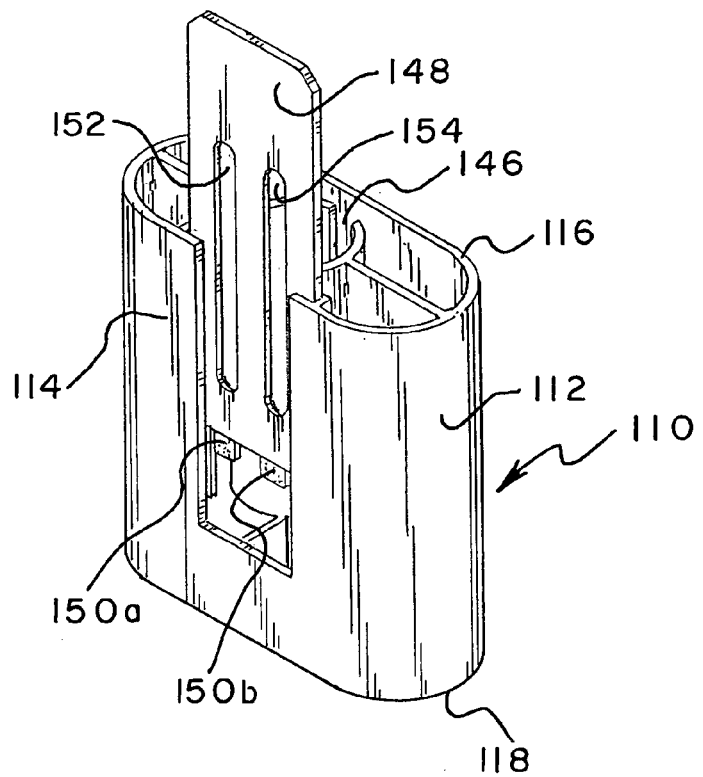
FIG. 6 is a front perspective view of a second embodiment of the present invention.
Figure 7:
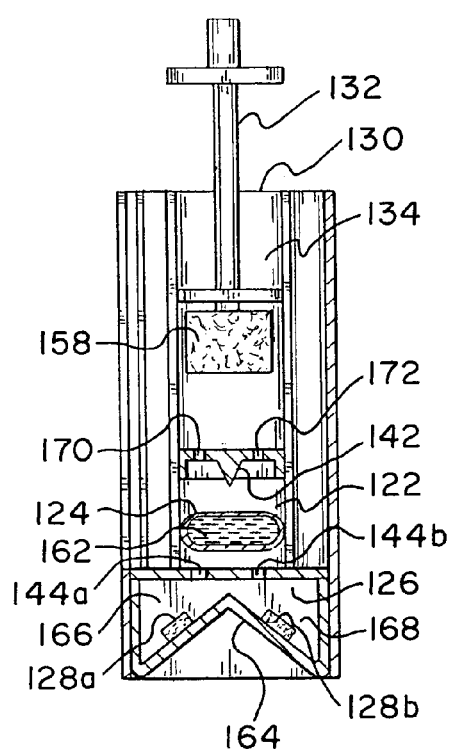
FIG. 7 is a cross-sectional view of the second embodiment of the present invention.

A second embodiment of the present invention is shown in FIGS. 6 and 7. This embodiment is similar in structure and function to the embodiment described above, with the differences discussed below. The device 110 essentially includes a housing 112 with a front side 114, a rear side 116, a bottom 118, and an open top. The housing 112 also includes a first chamber 122 for storing a pre-treatment reagent 124 and a second chamber 126 for storing second reagents, such as binders 128a and 128b. (See FIG. 7.) Located within the top of the housing 112 is an opening 130 through which a test sample collector 132 may be slidably mounted and a slot opening 146 through which an elongated holder member 148 for securing immunoassay test strips 150a and 150b may be slidably mounted.

The pre-treatment reagent is contained within a rupturable enclosure 162. A piercing member 142 is located within the first chamber 122 that is used to rupture the enclosure 162 in order to release the pre-treatment reagent 124 so that the sample and pre-treatment reagent form a mixture.

In order to use the device, the sample is collected on the sponge 158 and the collector 132 is inserted within the slot 134. The collector 132 is forced through the slot 134 so that is contacts the piercing member 142 which, in turn, ruptures the enclosure 162. Holes 170 and 172 are formed within the piercing member 142 so that the sample flows therethrough and mixes with the buffer. The sample and buffer mixture then flows through the apertures 144a and 144b formed in the bottom of the first chamber 122 and contacts the binders 128a and 128b. The second chamber 126 may have a partition 164 so that two separate compartments 166 and 168 are formed therein with a binder 128a and 128b located in a respective compartment 166 and 168. The partition 164 is formed in such a manner so that the sample and buffer mixture is split into the two compartments 166 and 168. The mixture and binder combination is incubated for a period of time.

Next, the elongated holder member 148 containing the test strips 150a and 150b is inserted through the opening 146 and slid downwardly, toward the bottom 118 of the housing 112. The test strips are typical prior art test strips where various antigens are dried thereon that compete with the analyte being tested for a binding site on the antibody. The slot 146 is in fluid communication with the second chamber 126 so that the test strips 150a and 150b are forced into contact with the mixture and binder combination as it is pushed toward the bottom 118 of the housing 112. Any reactions may be observed through the windows 152 and 154.

Figure 9:
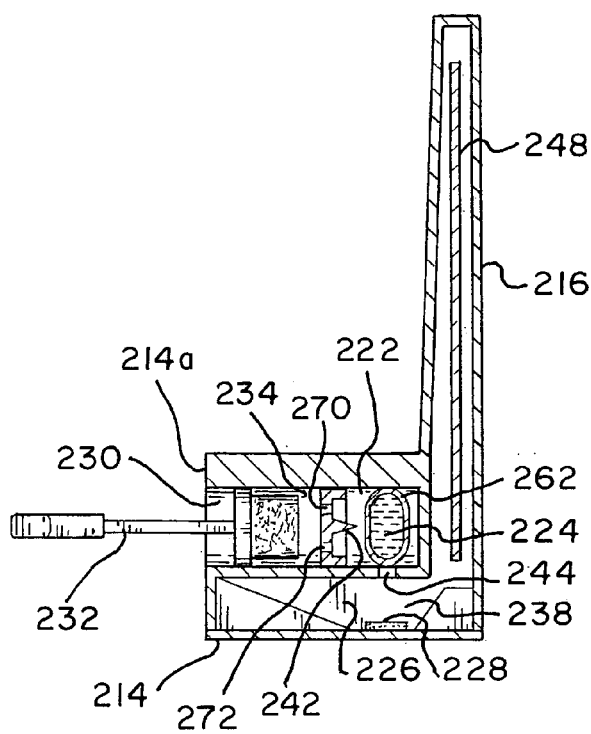
FIG. 9 is a cross-sectional view of the third embodiment of the present invention.
Figure 8:
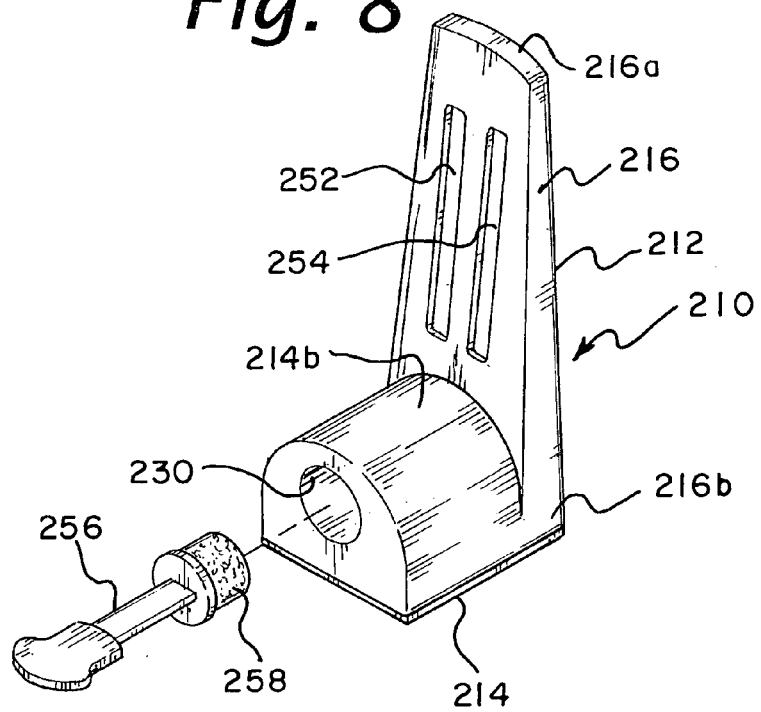
FIG. 8 is a front perspective view of a third embodiment of the present invention.
Figure 10:
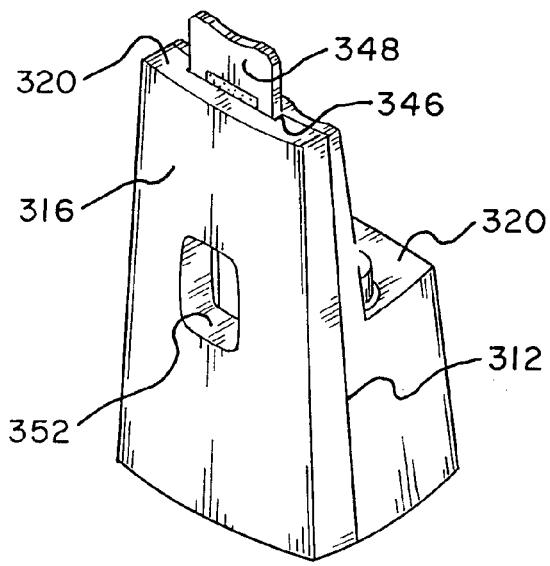
FIG. 10 is front perspective view of a fourth embodiment of the present invention.
Figure 11:
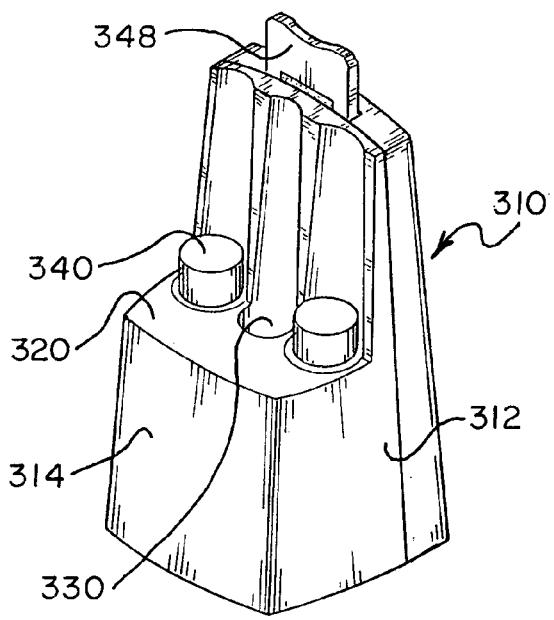
FIG. 11 is a rear perspective view of the fourth embodiment of the present invention.
Figure 12:
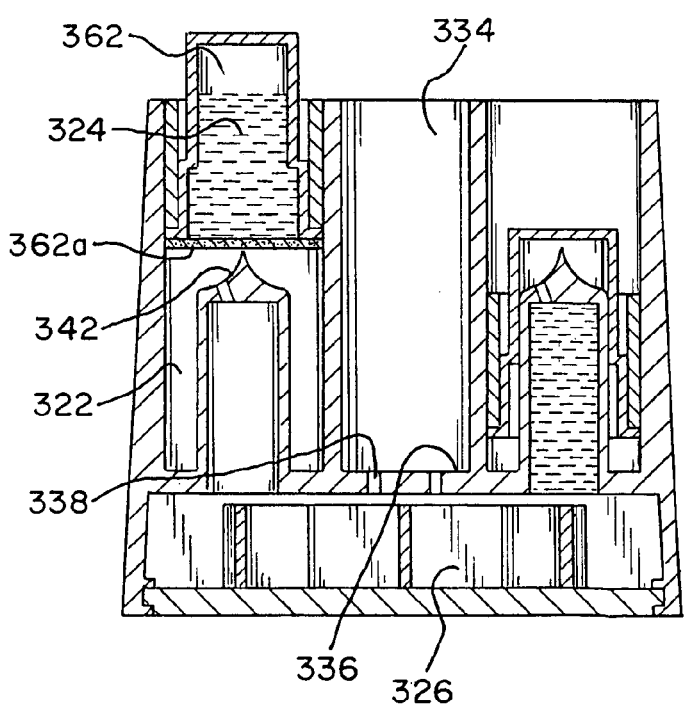
FIG. 12 is a partial cross-sectional view of the fourth embodiment.
Figure 13:
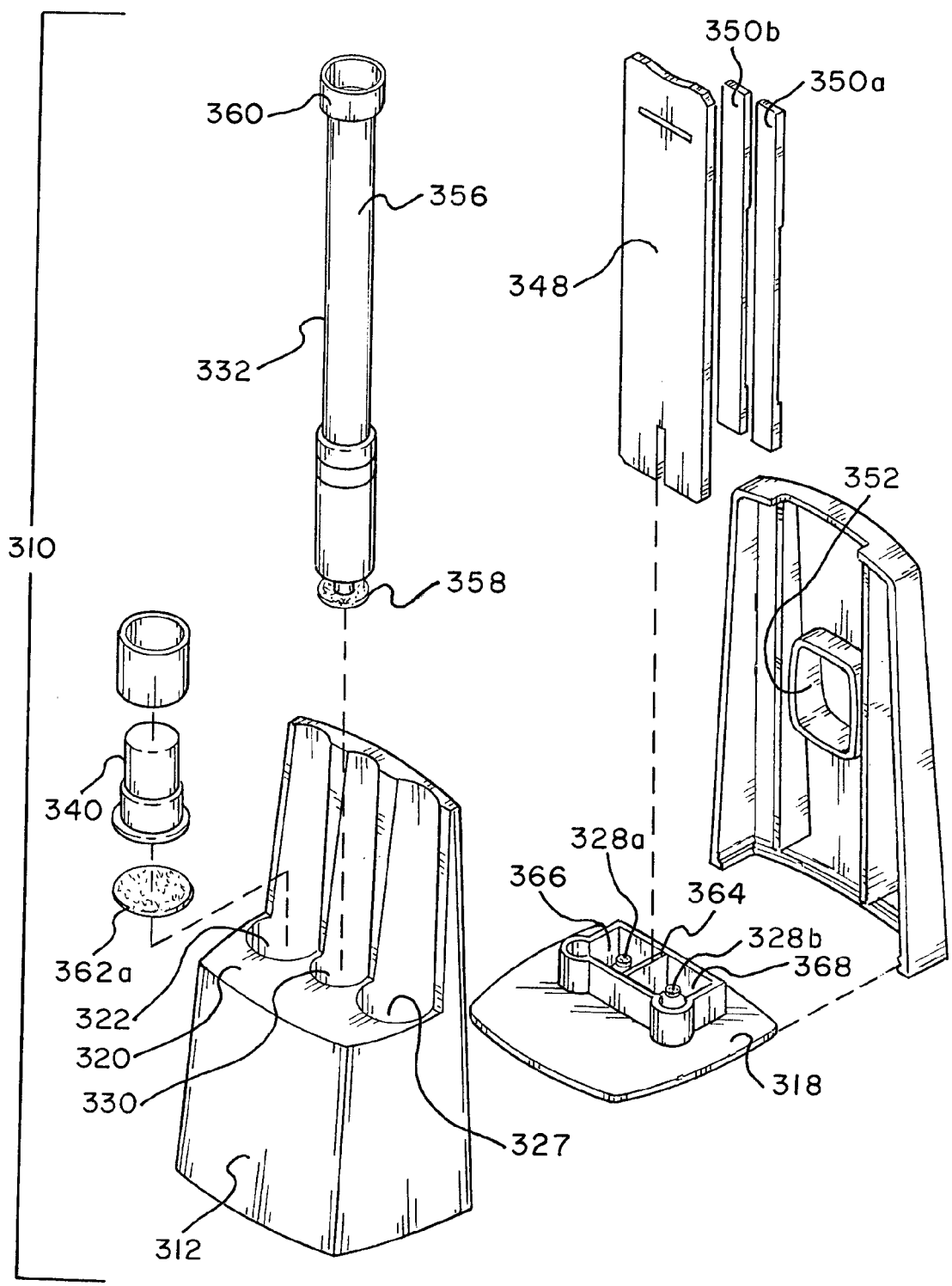
FIG. 13 is an exploded view of the fourth embodiment of the present invention.

A third embodiment of the present invention is shown in FIGS. 8 and 9. The device 210 is similar in structure and function to the embodiments described above, with the differences discussed below. In this embodiment the housing 212 is generally L-shaped, with a generally horizontal leg 214 and a generally vertical leg 216 with a top end 216a and a bottom end 216b. The horizontal leg 214 extends outwardly from the bottom end 216b of the vertical leg 216. The horizontal leg 214 has an open end 214a and an end 214b that joins with the vertical leg 216. The opening 230 for the elongated slot 234 for the sample collector 232 is located at the open end 214a of the horizontal leg 214.

As in the second embodiment, the piercing member 242 and first chamber 222 containing the buffer 224 are located within the slot 234. (FIG. 9.) Located within the vertical leg 216 is the test strip holder member 248. The front of the vertical leg 216 may have windows 252 and 254 formed therein. The second chamber 226 containing the second reagent 228 is in fluid communication with the first chamber 222 via apertures 244. The second chamber 226, however, is located adjacent the bottom of the horizontal leg 214.

In order to use the device, the sample is collected on the sponge 258 and the collector 256 is inserted within the slot 234. The collector 256 is forced through the slot 234 so that is contacts the piercing member 242 which, in turn, ruptures the bladder 262. Holes 270 and 272 are formed within the piercing member 242 so that the sample flows therethrough and mixes with the buffer. The sample and buffer mixture then flows through the aperture 244 and contacts the second reagent 228. The mixture and second reagent combination is incubated for a period of time.

The horizontal leg 214 is then raised upwardly so that the vertical leg 216 is titled backward. The positions of the horizontal and vertical legs are actually reversed so that the vertical leg is now horizontal and may rest on a flat surface. This action causes the mixture and binder combination to flow through the gap 238 between the second chamber 226 and the slot of the vertical leg 216 within which the test strip is contained. The combination contacts the test strip. Any reactions may be observed through the windows 252 and 254.

A fourth embodiment is shown in FIGS. 10–13. The device 310 is similar in structure and function to the embodiments described above, with the differences discussed below. The lateral flow immunoassay device essentially includes a housing 312 with a front side 314, a rear side 316, a bottom 318, and a top 320. The housing 312 also includes a first chamber 322 for storing a first, pre-treatment reagent 324 and a second chamber 326 for storing a second reagent 328a and 328b. (See FIGS. 12 and 13.) Located within the top 320 of the housing 312 is an opening 330 through which a test sample collector 332 may be slidably mounted. The opening 330 leads into an elongated slot 334 with a substantially closed bottom end 336. However, formed within the closed bottom end 336 is at least one opening 338 that allows for fluid communication with the second chamber 326. The housing 312 also includes a third chamber 327 which functions in the same manner as chamber 322 and will be described in greater detail below.

Also located in the front side 314 of the housing 312 is means 340 for activating the pre-treatment reagent 324. The activating means 340 fits within the first chamber 322 and may be in the form of a button. While the button 340 is shown protruding from the chamber 322, it may very well be recessed within the chamber in order to avoid inadvertent activation. Located at the bottom of the first chamber 322 is at least one aperture which enables the first chamber 322 to be in fluid communication with the second chamber 326. The operation of this button will be discussed in greater detail below. Located in the top 320 of the housing 312 is an elongated slit 346 through which an elongated holder member 348 for securing immunoassay test strips 350a and 350b, for example, may be slidably mounted. (See FIGS. 11 and 13.) The rear side 316 of the housing 312 has at least one widow 352 through which any reaction on the test strip may be observed. (See FIG. 11.)

The sample collector 332 may include an elongated member 356 with a swab or sponge 358 located at one end and a handle 360 located at the opposite end. (See FIG. 13.) The pre-treatment reagent may be a standard buffer and is contained within a rupturable enclosure or receptacle 362 which is located within the activating means 340. The receptacle 362 may be sealed with a rupturable seal 362a. The second reagent may be an antigen or a binder such as a colloidal gold-antibody complex, for example.

In order to use the device, a test sample is collected on the sponge 358. The collector 332 is then inserted through the opening 330 and into the slot 334. As the sponge 358 is forced through the slot 334, it contacts the opening 338 located at the bottom end 336 of the slot 334. The test sample is forced through the opening 338 and into the second chamber 326. Pressure is then applied to the button 340 using a tool which may be in the form of an elongated, generally cylindrical handle, such as the collector 332 in an inverted position. Alternatively, the button may be depressed simultaneously with, or before, the sponge is inserted through the slot. Located within the chamber 322 is a piercing member 342 that, as force is continued to be placed on the button 340, comes into contact with the rupturable seal 362a and ruptures it. The buffer flows through an aperture located in the first chamber 322. Sample flows through the opening 338 and mixes with the buffer 324.

The sample and buffer then flow into the second chamber 326 which is located adjacent the bottom 318 of the housing 312. The second chamber 326 may have a partition 364 so that two separate compartments 366 and 368 are formed therein with a second reagent 328a and 328b located in a respective compartment 366 and 368. The partition 364 is formed in such a manner so that the sample is split into the two compartments 366 and 368. The second reagent is introduced to the mixture and is allowed to react for a period of time. That is, the reagent and mixture combination is incubated for a period of time.

Next, the elongated holder member 348 containing the test strips 350a and 350b is inserted through the slit 346 and slid downwardly, toward the bottom 318 of the housing 312. The test strips 350a and 350b are typical prior art test strips where various antigens are dried thereon that compete with the analyte being tested for a binding site on the antibody. The slit 346 is in fluid communication with the second chamber 326 so that the test strips 350a and 350b are forced into contact with the mixture and second reagent combination as it is pushed toward the bottom 318 of the housing 312. Any reactions on the test strips 350a and 350b may be observed through the window 352.

The present invention may be embodied in other specific forms without departing from the spirit or essential attributes thereto and accordingly, reference should be made to the appended claims rather than to the foregoing specification as indicating the scope of the invention.

We claim:

1. A lateral flow immunoassay device comprising: a housing including means for holding a test sample collector with a test sample contained within said collector; an elongated holder member securing at least one immunoassay test strip therein; a first chamber containing a first, pre-treatment reagent; a second chamber containing a second reagent; means for contacting the test sample with said pre-treatment reagent and allowing said test sample to mix with said first reagent and to form a mixture; means for combining said second reagent with said mixture in the second chamber and allowing said mixture to react with said second reagent for a period of time prior to contacting the mixture and second reagent combination with at least one immunoassay test strip; means for holding said elongated holder member at a position spaced from the second chamber until said elongated holder member is activated; and means for allowing the mixture and second reagent combination to contact said at least one immunoassay test strip.

2. The lateral flow immunoassay device of claim 1 wherein said pre-treatment reagent includes a buffer solution.

3. The lateral flow immunoassay device of claim 1 wherein said second reagent is a binder.

4. The lateral flow immunoassay device of claim 3 wherein said binder is a colloid gold-antibody complex.

5. The lateral flow immunoassay device of claim 1 wherein said second reagent is an antigen.

6. The lateral flow immunoassay device of claim 1 wherein said pre-treatment reagent is contained within a rupturable enclosure.

7. The lateral flow immunoassay device of claim 6 wherein said contacting means includes a piercing member that ruptures said enclosure and releases said first reagent therefrom, the test sample being in fluid communication with said first reagent when the test sample is released from the sample collector.

8. The lateral flow immunoassay device of claim 1 wherein said introducing means includes apertures in communication with said second chamber through which said mixture flows and contacts said second reagent.

9. The lateral flow immunoassay device of claim 1 wherein said means for holding said elongated holder member prevents the test strip from contacting the mixture and second reagent combination until activated.

10. The lateral flow immunoassay device of claim 1 wherein said means for holding the test sample collector includes an elongated slot.

11. The lateral flow immunoassay device of claim 6 wherein said contacting means includes a button and a piercing member, said button activating said piercing member to rupture said enclosure and release said first reagent contained therein, the test sample being in fluid communication with said first reagent when the test sample is released from the sample collector.

12. The lateral flow immunoassay device of claim 1 wherein said housing is generally L-shaped with a vertical leg having a top end and a bottom end and a horizontal leg extending outwardly from said bottom of said vertical leg.

13. The lateral flow immunoassay device of claim 12 wherein said test strip is located within said vertical leg.

14. A lateral flow immunoassay device comprising:
a housing including means for holding a test sample collector with a test sample contained therein; an elongated holder member for securing at least one immunoassay test strip therein; a first chamber containing a first reagent; a second chamber containing a second reagent; means for permitting the test sample, the first reagent and the second reagent to mix in the second chamber prior to contacting the mixture of the first reagent, second reagent and test sample with a test strip; means for holding said elongated holder member at a position spaced from the second chamber until said elongated holder member is activated; and means for permitting said test sample, said test strip, said first reagent, and said second reagent to be in fluid communication.

15. The lateral flow immunoassay device of claim 14 wherein said first reagent is contained in a rupturable enclosure.

16. The lateral flow immunoassay device of claim 14 wherein said first reagent includes a buffer solution.

17. The lateral flow immunoassay device of claim 14 wherein said second reagent is a binder.

18. The lateral flow immunoassay device of claim 17 wherein said binder is a colloidal gold-antibody complex.

19. The lateral flow immunoassay device of claim 14 wherein said second reagent is an antigen.

20. The lateral flow immunoassay device of claim 15 further including a piercing member that ruptures said enclosure and releases said first reagent therefrom, the test sample being in fluid communication with said first reagent when the test sample is released from the sample collector.

21. The lateral flow immunoassay device of claim 14 further including apertures in communication with said second chamber through which said first reagent flows and contacts said second reagent.

22. The lateral flow immunoassay device of claim 14 wherein said means for holding the test sample collector includes an elongated slot.

23. The lateral flow immunoassay device of claim 15 further including a button and a piercing member, said button activating said piercing member to rupture said enclosure and to release said first reagent contained therein, the test sample being in fluid connection with said first reagent when the test sample is released from the sample collector.

24. The lateral flow immunoassay device of claim 14 wherein said housing is generally L-shaped with a vertical leg having a top end and a bottom end and a horizontal leg extending outwardly from said bottom of said vertical leg.

25. The lateral flow immunoassay device of claim 24 wherein said test strip is located within said vertical leg.

26. The lateral flow immunoassay device of claim 1 wherein the pre-treatment reagent dilutes or denatures interferants in the test sample.

27. The lateral flow immunoassay device of claim 14 wherein the first reagent dilutes or denatures interferants in the test sample.

* * * * *